United States Patent [19]

Jacobs

[11] 3,952,578
[45] Apr. 27, 1976

[54] SCANNING ULTRASONIC SPECTROGRAPH FOR FLUID ANALYSIS

[75] Inventor: John E. Jacobs, Evanston, Ill.

[73] Assignee: The United States of America as represented by the Secretary of the Department of Health, Education and Welfare, Washington, D.C.

[22] Filed: Oct. 7, 1974

[21] Appl. No.: 512,622

[52] U.S. Cl................................. 73/64.1; 73/67.6
[51] Int. Cl.².......................................... G01N 33/16
[58] Field of Search.................. 73/32 A, 64.1, 552, 73/558, 559, 560, 67.5, 67.6

[56] References Cited
UNITED STATES PATENTS

| 3,392,574 | 7/1968 | Lemon et al................ 73/67.5 R X |
| 3,568,661 | 3/1971 | Franklin......................... 73/67.6 X |
| 3,587,295 | 6/1971 | Simons.............................. 73/64.1 |

Primary Examiner—James J. Gill
Attorney, Agent, or Firm—Browdy and Neimark

[57] ABSTRACT

An apparatus for time delay acoustic spectrographic analysis of fluid composition uses frequency modulated ultrasonic vibrations which are transmitted through the fluid from a sending transducer to a receiving transducer. By scanning the frequency of the modulated vibrations at a sufficiently high rate, standing waves which give erroneous indications of fluid component concentrations, are eliminated. The frequency of the signal at the sending transducer is compared with that at the receiving transducer and a comparing means whose output is related to the frequency difference of the signal at the receiving transducer from the sending transducer measures the number of times this signal shifts 360° during a scanning period. This measurement is directly related to a property of the fluid being measured. The method and apparatus have particular application in the investigation of coagulation in human blood.

4 Claims, 7 Drawing Figures

FIG.1
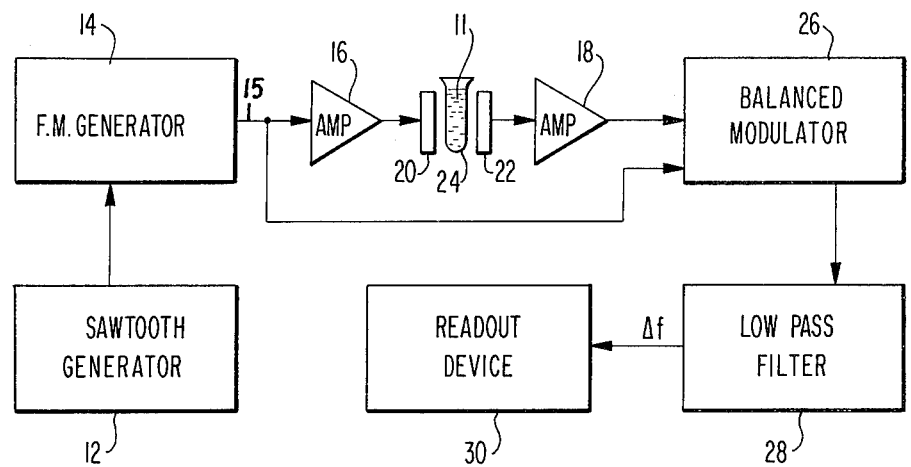
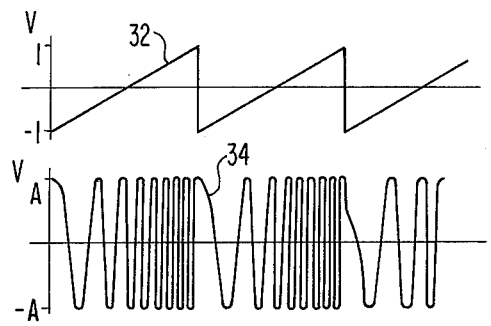
FIG.2
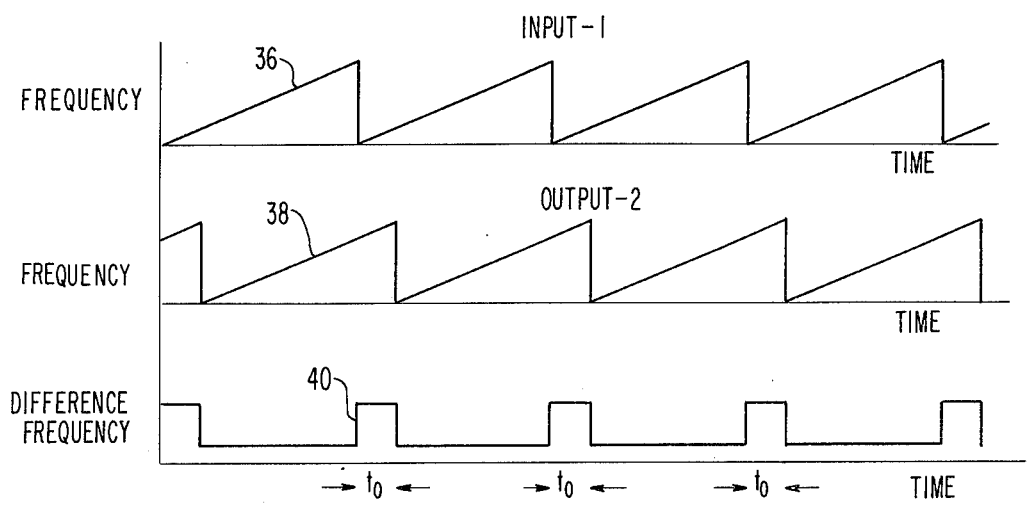
FIG.3

FIG.5
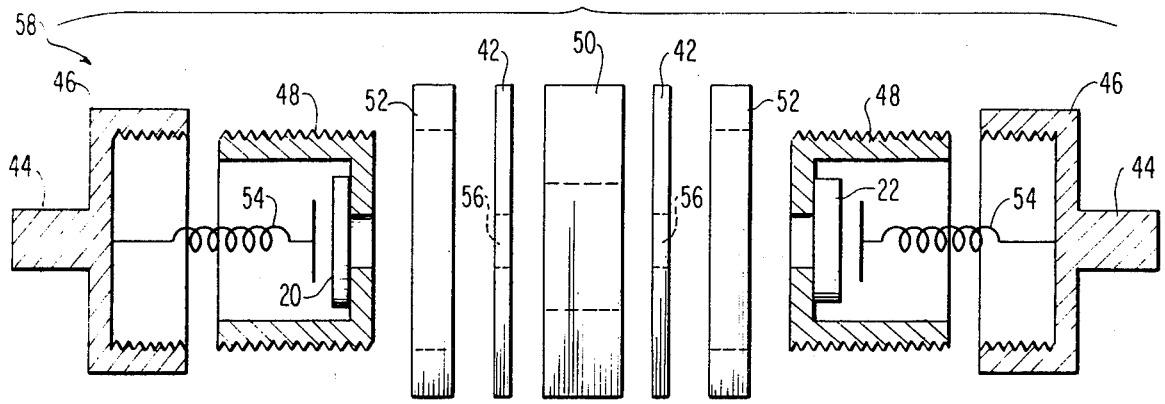
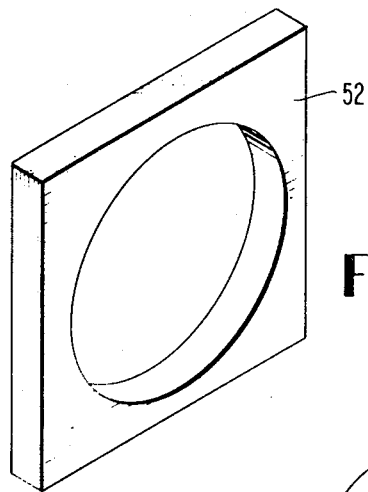
FIG.7
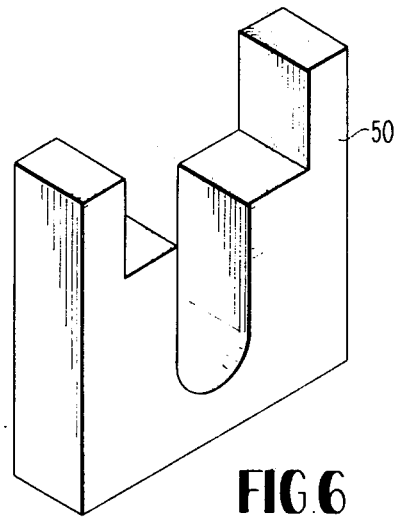
FIG.6
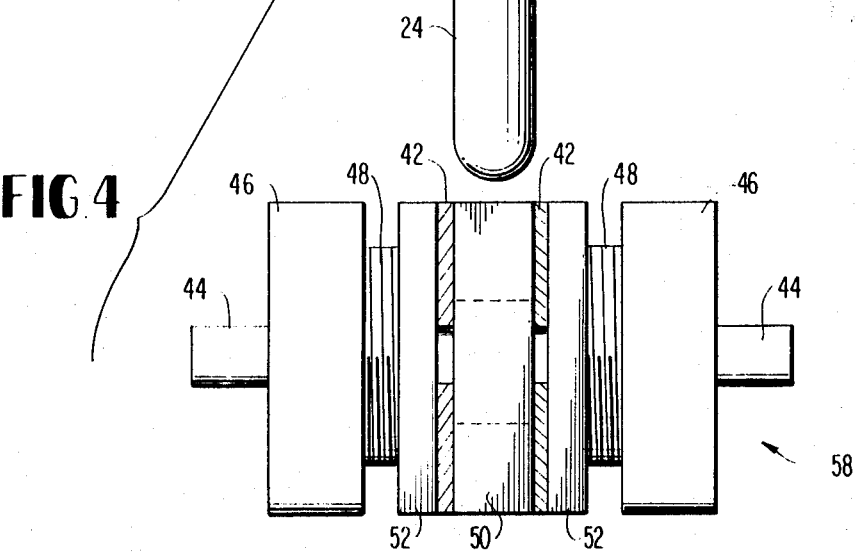
FIG.4

SCANNING ULTRASONIC SPECTROGRAPH FOR FLUID ANALYSIS

FIELD OF THE INVENTION

The invention relates to a method and apparatus for the spectrographic analysis of the composition of fluids by use of frequency modulated ultrasonic vibrations.

BACKGROUND OF THE INVENTION

Several methods and apparatus are available for the analysis of fluid composition based on investigation of the acoustic impedence of the fluid which changes with various fluid properties. These devices in general use either the measurement of the transit time through the fluid of pulses of acoustic energy or the measurement of the phase shift of a constant frequency acoustic wave energy signal applied to the fluid.

Using a fixed distance between the transducer for imparting the signal to the fluid and the transducer for receiving the signal after it transits the fluid simplifies instrumentation and reduces the possibility of error. With a single frequency system, however, a fixed transducer separation causes problems because of the effects of constructive and destructive interference (standing waves).

SUMMARY

In the frequency modulated system of the present invention, however, this problem is eliminated because the acoustic wave is continuously changing frequency thus giving rise to no major standing wave effects. The measurement of pulse transit time in the one form of the prior art involves generally complicated circuitry and apparatus. The difference frequency concept of the present invention uses a minimum amount of hardware and electronic components. Integrated circuit technology allows the construction of this precision scientific instrumentation with only a few discrete components. This gives the difference frequency technique much commercial appeal.

All types of pulse systems send a pulse of acoustic energy and clock its travel time. This gives a discrete velocity reading for that pulse only. It is not a continuous type of system and velocity changes which occur between pulses cannot be detected. The acoustic spectrograph of the present invention is by nature a continuous type of instrumentation and is capable of detecting a velocity change (within its sensitivity) during any time interval. The apparatus of the prior art do not possess the capacity to give a read-out in the form of spectral data, i.e. continuous velocity and phase versus frequency measurements. The acoustic spectrograph of the present invention does possess this capacity.

The use of the difference frequency measurement to obtain velocity information as shown in the present invention is a very promising form of laboratory instrumentation. It is capable of investigating the changes in fluid properties undergone by a fluid over a short period of time such as the coagulation of human blood.

It is therefore an object of the present invention to overcome the defects of the prior art, such as those indicated above.

It is another object to provide for the acoustic spectrographic analysis of fluids which eliminates standing wave problems of the prior art.

It is yet another object to provide for improved spectographic analysis.

It is a further object of the present invention to create a method and apparatus for acoustic spectrographic analysis of fluids which simplfies the instrumentation needed for such analysis.

A still further object of the present invention is to create a method and apparatus for acoustic spectrograph analysis of fluids capable of continuously monitoring the velocity of the acoustic energy through the fluid such that a fluid undergoing a rapid change in properties can be spectrographically analyzed during this change.

An additional object of the present invention is to create a method and apparatus for the acoustic spectrographic analysis of fluids capable of making spectral data available.

BRIEF DESCRIPTION OF THE FIGURES

The present invention can be more fully understood by reference to the following detailed description of an embodiment of the invention taken in conjunction with the figures wherein:

FIG. 1 shows a schematic diagram of an embodiment of the present invention;

FIG. 2 shows an output wave form of a saw-tooth generator and an FM generator of an embodiment of the present invention;

FIG. 3 shows the derivation of the difference frequency between the input and output transducer of an embodiment of the present invention;

FIG. 4 shows a side elevational partially cut away view of a sample housing of an embodiment of the present invention;

FIG. 5 shows an exploded side elevational view of the sample housing assembly of FIG. 4;

FIG. 6 shows a pictorial view of sample housing of FIG. 5; and

FIG. 7 shows a pictorial view of the transducer mount of FIG. 5.

DETAILED DESCRIPTION

With reference to FIG. 1 which shows a schematic diagram of the instrumentation of the present invention, the sample to be analyzed 11, which may be human blood undergoing a coagulation process, is placed in a sample container 24. Sample container 24 is mounted between the input transducer 20 and the output transducer 22 as will be further described hereinafter. A sawtooth generator 12 which is a relaxation oscillator provides a time varying voltage output as shown at 32 in FIG. 2 to the FM generator 14. The output of the sawtooth generator 12 is applied to the control electrode of the variable frequency generator 14 to modulate the output of the frequency modulated variable oscillator 14. The FM generator 14 may consist of an MC1544 voltage controlled oscillator integrated circuit with a linear frequency v. voltage characteristic of 2.75 mhz/volt. The result is that a signal appears on the output electrode 15 which is a time-varying frequency signal with a linear increase in frequency during each cycle of the sawtooth generator voltage output, as shown in FIG. 2 at 34. The scanning rate produced by the frequency of the sawtooth wave generator 12 can be from 2 to 3 khz. The modulated output of the FM generator 14 varies from 3.5 to 6.5 Mhz as the output voltage of the sawtooth wave generator increases in magnitude during each scan.

The output of the FM generator 14 is applied to a transmission amplifier 16 and also to one input of the balanced modulator 26. The amplified signal from transmission amplifier 16 is applied to input transducer 20 and converted to an acoustic frequency modulated vibration which is transmitted through the sample fluid 11 to output transducer 22. The acoustic signal received at output transducer 22 is converted to an electrical signal which is amplified by receiving amplifier 18. The output of amplifier 18 is applied to a second input to the balanced modulator 26.

The choice of transducers used for an ultrasonic spectrograph system must center around the response characteristics of the transducers. The features to look for are the undamped resonant frequency and a relatively low Q. The low Q tends to give a broad flat frequency response. The piezeoelectric transducers used in the present invention are preferably barium titinate, e.g. those made by Transducer Products under the name LTZ-2. LTZ-2 is a ¾ inch diameter disc transducer, with a silver electrode on both sides for electrical contact, for operation as a piston source vibrator.

A barium titinate disc transducer has a distinct area of maximum efficiency centered around its resonant frequency. Since two transducers are in this system, an input transducer 20 and an output transducer 22, the response characteristics of the two must be multiplied to obtain the overall system response. In order to flatten the response characteristic of the system, the input and output transducers are chosen with different resonant frequencies, 3 and 5 Mhz respectively. This combination produces a good frequency response over the ranges used in this invention.

The balanced modulator 26 consists of a U987 integrated circuit and functions to convert the two input signals representative of the frequency of the output of the FM generator 14 and the receiving amplifier 18, and therefore also the frequency of the signal at the input transducer and the output transducer, to give an output from the balanced modulator representative of the sum and the difference of the frequency of these two signals. The output signal of the balanced modulator is applied to a low pass filter 28 which removes the signal representative of the sum of the frequency of the signals applied to the input transducer and the signal received at the output transducer. The signal passed by the low pass filter and applied to the output thereof is thus representative of the difference between the frequency at the input transducer and the output transducer. This signal is applied to a read-out device 30 discussed further herein. The magnitude of the difference frequency signal is dependent upon the time delay of the acoustic wave in the sample and is therefore a function of the velocity of sound in the sample.

As shown in FIG. 3, the input and output transducers have identical frequency versus time functions, however, the output frequency versus time lags in phase behind the input frequency versus time wave form. This is due to the acoustic impedance of the sample fluid.

It has long been known that characteristics of fluid can be related to the acoustic impedence thereof. Thus, the transit time of the acoustic wave between the transducers is related to the characteristics of the fluid to be measured. As shown in FIG. 3, the difference frequency is constant over much of the period of the sawtooth waves except during the portion labeled $t_o$. The value of $t_o$ is equal to the distance between the transducers divided by the velocity of sound in the sample and thus is equal to the transit time of the acoustic wave between the transducers. Where the distance between the transducers is fixed $t_o$ and consequently the difference frequency are dependent upon the velocity of sound in the sample.

Various means of reading the difference frequency shown as the readout device 30 in FIG. 1, can be used. One possibility is the use of a digital Hewlett Packard No. 5212A electronic frequency counter. The output of the low pass filter is fed into the input of the frequency counter and a numerical count of the frequency is displayed. A second possible means used as the readout device 30 can be a phase lock loop. When in lock, the phase lock acts like a linear frequency to voltage converter. Therefore the output voltage is linearly proportional to the input frequency. This output voltage is recorded on a Brush Mark 280 strip chart recorder.

The sensitivities of these two alternate readout devices are respectively 4% and 1%. These sensitivity figures refer to the minimum increments in velocity change that can be detected with the acoustic spectrograph of the present invention using the particular readout device.

Referring to FIG. 4, the sampling assembly of the present device is shown. Sample container 24 is placed in a slot in sample housing 50. This slot is located between acoustic insulators 42. These acoustic insulators 42 may be of cork, water or glycerine or other suitable material of known acoustic impedence. Transducer mounting plates 52 are located adjacent the acoustic insulating material 42 on opposite sides of the sample container 24. The combined transducer housing 46, 48 is mounted in the transducer mounting plate. Electrical connectors 44 supply electrical power to the transducers 20, 22 located within the transducer housing 46, 48.

The construction of the sampling assembly of the present invention can be more fully understood by reference to FIG. 5 which is an exploded side-elevational view of the sampling assembly of the present invention. In this figure like numbers correspond to identical components shown in FIG. 4. Also shown in the exploded pictorial view of FIG. 5 are the input 20 and output 22 transducers. Windows 56 in the acoustic insulators 42 allow for passage of the acoustic energy from input transducer 20 through the sample mounted in the sample housing 50 to the output transducer 22. Also shown are the transducer electrodes 54 which connect the electrical connectors 44 to the transducers 20 and 22.

FIGS. 6 and 7 show pictorial views of respectively the sample housing 50 shown in FIGS. 4 and 5 and the transducer mounting plate 52 shown also in FIGS. 4 and 5.

It will be understood that the embodiments of the present invention herein shown are only for the purpose of illustration and are not to be considered to limit the invention beyond the scope of the following claims.

What is claimed is:

1. A scanning acoustic spectrographic analyser for time delay acoustic spectrography in investigating the changes in fluid properties undergone by a fluid in a short period of time comprising:

signal generating means for generating a frequency modulated first electrical signal having a periodic linear increase in frequency;

first transducer means for converting said frequency modulated first electrical signal into an acoustic wave signal and transmitting said acoustic wave signal through the fluid to be analyzed, wherein said first transducer means transmits but does not receive acoustical signals;

second transducer means for receiving said acoustic wave signal transmitted through the fluid and coverting said received acoustic wave signal to a second electrical signal, wherein said second transducer means receives, but does not transmit acoustical signals;

comparing means, having as first and second inputs said first and second electrical signals, for comparing said first and second electrical signals and generating an output signal dependent upon the difference in frequency between said first and second electrical signals;

display means for displaying said output signal in visual form.

2. A scanning acoustic spectropraphic analyser of claim 1 wherein said signal generating means includes:
 a sawtooth wave generating means for generating a periodic sawtooth wave signal; and
 a frequency modulating means, having a control terminal electrically connected to said periodic sawtooth wave signal, for generating a frequency modulated signal having a periodic linear increase in frequency.

3. The scanning acoustic spectrographic analyser of claim 1 wherein the fluid is coagulating human blood.

4. An analyzer in accordance with claim 1 wherein said second transducer means is disposed directly opposite said first transducer means.

* * * * *